US011826455B2

(12) United States Patent
Shiroya et al.

(10) Patent No.: US 11,826,455 B2
(45) Date of Patent: *Nov. 28, 2023

(54) SELF-HEALING OR SELF-REPAIRING FILM FORMING COMPOSITION

(71) Applicant: L'OREAL, Paris (FR)

(72) Inventors: Toshifumi Shiroya, Kawasaki (JP); Takehiko Kasai, Kawasaki (JP); Hidehiko Asanuma, Kawasaki (JP); Tomomi Hamazaki, Kawasaki (JP); Toru Koike, Kawasaki (JP)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/268,398

(22) PCT Filed: Aug. 9, 2019

(86) PCT No.: PCT/JP2019/032207
§ 371 (c)(1),
(2) Date: Feb. 12, 2021

(87) PCT Pub. No.: WO2020/045134
PCT Pub. Date: Mar. 5, 2020

(65) Prior Publication Data
US 2021/0177725 A1  Jun. 17, 2021

(30) Foreign Application Priority Data
Aug. 30, 2018 (JP) ................. 2018-161327

(51) Int. Cl.
| A61K 8/73 | (2006.01) |
| A61K 8/19 | (2006.01) |
| A61K 8/365 | (2006.01) |
| A61K 8/06 | (2006.01) |
| A61K 8/40 | (2006.01) |
| A61K 8/55 | (2006.01) |
| A61Q 17/04 | (2006.01) |
| A61Q 19/00 | (2006.01) |

(52) U.S. Cl.
CPC ............. *A61K 8/731* (2013.01); *A61K 8/06* (2013.01); *A61K 8/19* (2013.01); *A61K 8/365* (2013.01); *A61K 8/40* (2013.01); *A61K 8/55* (2013.01); *A61Q 17/04* (2013.01); *A61Q 19/00* (2013.01); *A61K 2800/5424* (2013.01); *A61K 2800/5426* (2013.01)

(58) Field of Classification Search
None
See application file for complete search history.

(56) References Cited

U.S. PATENT DOCUMENTS

| 2003/0022799 A1 | 1/2003 | Alvarado |
| 2004/0191199 A1 | 9/2004 | Mougin |
| 2004/0235693 A1 | 11/2004 | Wei |
| 2009/0175808 A1 * | 7/2009 | Galley ............... A61Q 5/00 514/3.7 |
| 2013/0178508 A1 | 7/2013 | Shirai |
| 2013/0280174 A1 | 10/2013 | Lipic et al. |
| 2014/0335039 A1 | 11/2014 | Merat |
| 2015/0093348 A1 | 4/2015 | Sato |
| 2015/0272865 A1 | 10/2015 | Mette |
| 2017/0326041 A1 | 11/2017 | Tsuzuki |
| 2018/0344618 A1 | 12/2018 | Motornov |

FOREIGN PATENT DOCUMENTS

| CN | 1780600 | 5/2006 |
| CN | 101155842 A | 4/2008 |
| CN | 103313699 | 9/2013 |
| CN | 108366915 | 8/2018 |
| CN | 108367175 | 8/2018 |
| DE | 102010029628 | 12/2010 |
| DE | 102012222771 | 6/2014 |
| EP | 0256691 A2 | 2/1988 |
| EP | 1593371 A1 * | 11/2005 ............. A61K 8/345 |
| EP | 2022480 A1 | 2/2009 |
| EP | 2022482 A1 | 2/2009 |
| FR | 2881955 A1 | 8/2006 |
| JP | 2006273855 | 10/2006 |
| JP | 2010285432 | 12/2010 |
| JP | 2016113405 | 6/2016 |
| KR | 10-2014-0105728 A | 9/2014 |
| WO | 2012038534 A1 | 3/2012 |

(Continued)

OTHER PUBLICATIONS

Taylor, D.L., et al., "Self-Healing Hydrogels," Advanced Materials, 2016, 28, 9060-9093.
Huang, Y., et al., "Self-Assembly of Stiff, Adhesive and Self-Healing Gels from Common Polyelectrolytes," Langmuir, 2014, 30, 7771-7777.
International Search Report dated Feb. 12, 2019, issued in corresponding International Application No. PCT/JP2019/032207, filed Aug. 9, 2019.
Office Action dated Jun. 6, 2022, issued in corresponding Japanese Application No. 2018-161327, filed on Aug. 30, 2018, 13 pages.
Mintel, "Peeling Mask", https://www.gnpd.com, ID: 1868355, 2012, 3 pages (with partial translation).
Mintel, "Purifying Toner", https://www.gnpd.com, ID: 1007859, 2008 3 pages (with partial translation).

(Continued)

*Primary Examiner* — Jennifer A Berrios
(74) *Attorney, Agent, or Firm* — CHRISTENSEN O'CONNOR JOHNSON KINDNESS PLLC

(57) ABSTRACT

The present invention relates to a composition comprising (a) at least one cationic polysaccharide; (b) at least one crosslinker having three or more acid groups or salt thereof; and (c) at least one physiologically acceptable volatile medium, wherein the composition optionally comprises surfactant(s) in an amount of 1% by weight or less, preferably 0.5% by weight or less, and more preferably 0.3% by weight or less, relative to the total weight of the composition. The composition according to the present invention can provide a self-healing or self-repairing film.

12 Claims, No Drawings

(56) References Cited

FOREIGN PATENT DOCUMENTS

| WO | 2013069165 | 5/2013 |
|---|---|---|
| WO | 2016098786 | 6/2016 |

OTHER PUBLICATIONS

Office Action dated Sep. 7, 2022, issued in corresponding Chinese Application No. 201980055963.2, filed on Aug. 9, 2019 20 pages.
Wang, Shenmin, "Chemistry of Daily Chemicals Formula Design and Production Process of Daily Chemicals"; Harbin Institute of Technology Press, Aug. 31, 2001, pp. 129-130.
Second Office Action dated Jan. 28, 2023, issued in corresponding Chinese Application No. 201980055963.2, filed Aug. 9, 2019, 18 pages.
Zhong, P. et al., "Biochemicals Production Technology," Jiangxi Science & Technology Publishing House, May 31, 2007 pp. 335-336.
Neo for Men 3x1 Multi-Functional Total Fresh Hair Body Beard Conditioning Shampoo (ID: 5083533), Mintel GNPD [online], Sep. 2017, [search date; May 23, 2022], Ingredients, Description of goods and Contents of appeal, <https://www.gnpd.com>, 4 pages.
Strengthening & Darkening Essence Oil Shampoo (ID: 3664321), Mintel GNPD [online], Dec. 2015, [search date; May 23, 2022], Ingredients, Description of goods and Contents of appeal, <https://www.gnpd.com>, 4 pages.
Whip Cream Shampoo (ID: 5765605), Mintel GNPD [online], Jun. 2018, [search date; May 23, 2022], Ingredients, Description of goods and Contents of appeal, <https://www.gnpd.com>, 5 pages.
International Search Report dated Dec. 2, 2019, issued in corresponding International Application No. PCT/JP2019/032208, filed Aug. 9, 2019, 3 pages.
Japanese Office Action dated Jun. 6, 2022, issued in related Japanese Application No. 2018-161328, 13 pages.
International Search Report dated Nov. 20, 2019, issued in corresponding international Application PCT/JP2019/032929, filed Aug. 16, 2019, 3 pages.
Notice of Reasons for Refusal dated Jun. 6, 2022, issued in corresponding Japanese Application No. 2018-161330, 10 pages.
First Chinese Office Action dated Sep. 29, 2022, issued in corresponding Chinese Application No. 2019800525886, filed Aug. 16, 2019, 17 pages.
First Office Action dated Sep. 6, 2022, issued in related Chinese Application No. 201980055675.7, filed Aug. 9, 2019, 20 pages.
Notice of Allowance dated Jul. 24, 2023, issued in corresponding Chinese Application No. 201980052588.6, filed Aug. 16, 2019, 7 pages.
Wu, W., et al., "Principle and application of emulsion and foam systems stabilized by particles. VI. Application of particle—stabilized emulsions and foams," China Surfactant Detergent & Cosmetics, vol. 43, No. 6, Dec. 2013, pp. 418-423.
Notice of Allowance dated Jul. 20, 2023, issued in corresponding Korean Application No. 10-2021-7003450, filed Aug. 16, 2019, 4 pages.
Office Action dated Sep. 13, 2023, issued in corresponding European Application No. 19763113.8, filed Aug. 9, 2019, 4 pages.
Office Action dated Oct. 2, 2023, issued in corresponding U.S. Appl. No. 17/271,158, filed Feb. 24, 2021, 32 pages.
Database GNPD [Online], MINTEL; May 29, 2015 (May 29, 2015), anonymous: "Double Header Shampoo + Conditioner", XP055627712, Database accession No. 355321 1; 3 pages.

\* cited by examiner

SELF-HEALING OR SELF-REPAIRING FILM FORMING COMPOSITION

TECHNICAL FIELD

The present invention relates to a composition including a dynamically and ionically-crosslinked (DIC) gel.

BACKGROUND ART

Nowadays, there are plenty of scientific reports about self-healing hydrogels (e.g., Adv. Mater. 2016, 28, 9060-9093, Daniele Lynne et al., "Self-Healing Hydrogels"). Especially, a self-healing gel composed of a polyelectrolyte (polyallylamine) and a crosslinker (tripolyphosphate) is disclosed in "Self-assembly of stiff, adhesive and self-healing gels from common polyelectrolytes", (Langmuir, 2014, 30, 7771).

DISCLOSURE OF INVENTION

If cosmetic products have self-healing or self-repairing properties, it is expected that the cosmetic films prepared by the cosmetic products would be automatically repaired even though the cosmetic films are broken due to, for example, scratching and the like, and therefore, long lastingness of cosmetic effects provided by the cosmetic films would be dramatically improved.

Thus, the objective of the present invention is to provide a composition which can provide a self-healing or self-repairing film which would be useful for cosmetic applications.

The above objective of the present invention can be achieved by a composition comprising:

(a) at least one cationic polysaccharide;

(b) at least one crosslinker having three or more acid groups or salt thereof; and (c) at least one physiologically acceptable volatile medium, wherein the composition optionally comprises surfactant(s) in an amount of 1% by weight Or less, preferably 0.5% by weight or less, and more preferably 0.3% by weight or less, relative to the total weight of the composition.

The (a) cationic polysaccharide may be selected from cationic cellulose polymers.

The (a) cationic polysaccharide may have at least one quaternary ammonium group.

The (a) cationic polysaccharide may be selected from the group consisting of polyquaternium-4, polyquaternium-10, polyquaternium-24, polyquaternium-67, and a mixture thereof.

The amount of the (a) cationic polysaccharide(s) in the composition according to the present invention may be from 0.01% to 20% by weight, preferably from 0.1% to 15% by weight, and more preferably from 0.5% to 10% by weight, relative to the total weight of the composition.

The (b) crosslinker having three or more acid groups or salt thereof may be selected from non-polymeric organic acids having three or more acid groups and salts thereof.

The (b) crosslinker having three or more acid groups may have three or more acid groups selected from the group consisting of a carboxylic group, a sulfuric group, a sulfonic group, a phosphonic group, phosphoric group, a phenolic hydroxyl group, and a mixture thereof.

The (b) crosslinker having three or more acid groups or salt thereof may be selected from the group consisting of phytic acid, citric acid, aconitic acid, EDTA, glycyrrhizin, inositol triphosphate, inositol pentakisphosphate, tripolyphosphate, adenosine triphosphate, a salt thereof, and a mixture thereof.

The amount of the (b) crosslinker(s) having three or more acid groups or salt(s) thereof in the composition according to the present invention may be from 0.001% to 15% by weight, preferably from 0.05% to 10% by weight, and more preferably from 0.1% to 5% by weight, relative to the total weight of the composition.

The amount of the (c) physiologically acceptable volatile medium(s), preferably water, in the composition according to the present invention may be from 50% to 99% by weight, preferably from 60% to 98% by weight, and more preferably from 70% to 97% by weight, relative to the total weight of the composition.

The composition according to the present invention may further comprise (d) at least one anionic polymer.

The composition according to the present invention may further comprise at least one oil and/or at least one organic UV filter. The amount of the oil(s) and/or the organic UV filter(s) in the composition according to the present invention may be less than 10% by weight, preferably less than 5% by weight, and more preferably less than 1% by weight, relative to the total weight of the composition. In this case, the composition according to the present invention may be in the form of an emulsion.

The composition according to the present invention may be a cosmetic composition, preferably a skin cosmetic composition.

The present invention also relates to a cosmetic process for a keratin substance such as skin, comprising applying to the keratin substance the composition according to the present invention, and drying the composition to form a cosmetic film on the keratin substance.

BEST MODE FOR CARRYING OUT THE INVENTION

After diligent research, the inventors have discovered that it is possible to provide a composition which can provide a self-healing or self-repairing film which would be useful for cosmetic applications. Thus, the composition according to the present invention comprises:

(a) at least one cationic polysaccharide;

(b) at least one crosslinker having three or more acid groups or salt thereof; and (c) at least one physiologically acceptable volatile medium, wherein the composition optionally comprises surfactant(s) in an amount of 1% by weight or less, preferably 0.5% by weight or less, and more preferably 0.3% by weight or less, relative to the total weight of the composition.

The composition according to the present invention can provide a self-healing or self-repairing film. In other words, the film provided by the composition according to the present invention can be automatically repaired even though the film is broken due to, for example, scratching and the like, and therefore, long lastingness of cosmetic effects provided by the film can be improved.

The self-healing or self-repairing film can be composed of a gel, preferably a hydrogel. The gel is dynamically and ionically-crosslinked. The dynamically and ionically-crosslinked gel prepared by the composition according to the present invention is abbreviated as a DIC-gel.

The dynamic and ionic-crosslinking in the DIC-gel is different from permanent covalent bonding because it is breakable but reformable. The dynamic and ionic-crosslinking can be easily broken by, for example, cutting and the like, but can be easily reformed by, for example, contacting each other, thereby exhibiting self-healing or self-repairing properties. For example, if the gel is cut into two pieces, the ionic interaction between the cationic polymer and the crosslinker breaks. However, if the two pieces contact each other, they can reform ionic-bonding between the cationic polymer and the crosslinker, and they can adhere to each other. Therefore, even if cracks, for example, are formed on the gel, they can disappear.

In one embodiment, the self-healing or self-repairing gel provided by the composition according to the present invention can be used as a filler. For example, the gel can be filled in wrinkles on the skin, in particular, the face. Even if the gel filled in the wrinkles breaks into pieces due to movements of the wrinkles due to, for example, smiling, they can then be automatically repaired by adhering to each other. Thus, the wrinkles can be less noticeable for a long period of time.

The composition according to the present invention is stable for a long period of time, and can be used to easily prepare a film of a gel which has self-healing or self-repairing properties by applying the composition onto a substrate, preferably a keratin substrate such as skin, and drying the composition.

The film prepared by the composition according to the present invention can have a variety of cosmetic functions.

For example, the film itself prepared by the composition according to the present invention may have cosmetic effects such as absorbing or adsorbing malodor, changing the appearance of a keratin substrate such as skin, changing the feel to the touch of the keratin substrate, and/or protecting the keratin substrate from, for example, dirt or pollutants.

If the film prepared by the composition according to the present invention includes at least one cosmetic active ingredient, the film can have cosmetic effects provided by the cosmetic active ingredient(s). For example, if the film includes at least one cosmetic active ingredient selected from anti-aging agents, anti-sebum agents, deodorant agents, anti-perspirant agents, whitening agents and a mixture thereof, the film can treat the ageing of the skin, absorb sebum on the skin, control odors on the skin, control the perspiration on the skin, and/or whiten of the skin. For example, if the film prepared by the composition according to the present invention includes a UV filter, the film can show UV shielding effects which can be long lasting.

If the composition according to the present invention includes at least one anionic polymer, the elasticity of the gel can be tuned by the addition of the anionic charges by the anionic polymer. The incorporation of the anionic polymer may make the gel tougher.

Hereinafter, the composition, process and the like according to the present invention will be explained in a more detailed manner.

(Cationic Polysaccharide)

The composition according to the present invention includes (a) at least one cationic polysaccharide. Two or more different types of (a) cationic polysaccharides may be used in combination. Thus, a single type of (a) cationic polysaccharide or a combination of different types of (a) cationic polysaccharides may be used.

The (a) cationic polysaccharide has a positive charge density. The charge density of the (a) cationic polysaccharide may be from 0.01 meq/g to 20 meq/g, preferably from 0.05 to 15 meq/g, and more preferably from 0.1 to 10 meq/g.

It may be preferable that the molecular weight of the (a) cationic polysaccharide be 500 or more, preferably 1,000 or more, more preferably 2,000 or more, and even more preferably 5,000 or more.

Unless otherwise defined in the description, "molecular weight" means a number average molecular weight.

The (a) cationic polysaccharide may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group. The term (primary) "amino group" here means the group —$NH_2$. It is preferable that the (a) cationic polysaccharide have at least one quaternary ammonium group.

The (a) cationic polysaccharide may be a homopolymer or a copolymer. The term "copolymer" is understood to mean both copolymers obtained from two kinds of monomers and those obtained from more than two kinds of monomers, such as terpolymers obtained from three kinds of monomers.

The (a) cationic polysaccharide may be selected from natural and synthetic cationic polysaccharides.

It is preferable that the (a) cationic polysaccharide be selected from cationic cellulose polymers. Non-limiting examples of the cationic cellulose polymers are as follows.

(1) Cationic cellulose polymers such as cellulose ether derivatives comprising one or more quaternary ammonium groups described, for example, in French Patent No. 1 492 597, such as the polymers sold under the names "JR" (JR 400, JR 125, JR 30M) or "LR" (LR 400, LR 30M) by the company Dow Chemical. These polymers are also defined in the CTFA dictionary as quaternary ammoniums of hydroxyethylcellulose that have reacted with an epoxide substituted with a trimethylammonium group.

(2) Cationic cellulose polymers such as cellulose copolymers and cellulose derivatives grafted with at least one water-soluble monomer of quaternary ammonium, and described, for example, in U.S. Pat. No. 4,131,576, such as hydroxyalkylcelluloses, for instance, hydroxymethyl-, hydroxyethyl-, and hydroxypropylcelluloses grafted, for example, with at least one chosen from methacryloylethyltrimethylammonium, methacrylamidopropyltrimethylammonium, and dimethyldiallylammonium. Commercial products corresponding to these polymers include, for example, the products sold under the names "Celquat® L 200" and "Celquat® H 100" by the company Akzo Novel.

(3) Cationic cellulose polymers having at least one quaternary ammonium group comprising at least one fatty chain, such as alkyl, arylalkyl or alkylaryl groups comprising at least 8 carbon atoms. It may be preferable that the cationic cellulose polymers be quaternized hydroxyethyl celluloses modified with at least one quaternary ammonium group comprising at least one fatty chain, such as alkyl, arylalkyl or alkylaryl groups comprising at least 8 carbon atoms, or mixtures thereof. The alkyl radicals borne by the quaternary ammonium group may preferably contain from 8 to 30 carbon atoms, especially from 10 to 30 carbon atoms. The aryl radicals preferably denote phenyl, benzyl, naphthyl or anthryl groups. More preferably, the cationic cellulose polymer may comprise at least one quaternary ammonium group including at least one $C_8$-$C_{30}$ hydrocarbon group. Examples of quaternized alkylhydroxyethylcelluloses containing $C_8$-$C_{30}$ fatty chains that may be mentioned include the products Quatrisoft LM 200, Quatrisoft LM-X 529-18-A, Quatrisoft LM-X 529-18B (C12 alkyl) and Quatrisoft LM-X 529-8 (C18 alkyl) or Softcat Polymer SL100, Softcat SX-1300X, Softcat SX-1300H, Softcat SL-5, Softcat SL-30, Softcat SL-60, Softcat SK-MH, Softcat SX-400X, Softcat SX-400H, SoftCat SK-L, Softcat SK-M, and Softcat SK-H, sold by the company Dow Chemical, and the products Crodacel QM, Crodacel, QL (C12 alkyl) and Crodacel QS (C18 alkyl) sold by the company Croda.

It is preferable that the (a) cationic polysaccharide be selected from the group consisting of polyquaternium-4, polyquaternium-10, polyquaternium-24, polyquaternium-67, and a mixture thereof.

The amount of the (a) cationic polysaccharide(s) in the composition according to the present invention may be 0.01% by weight or more, preferably 0.1% by weight or more, and more preferably 0.5% by weight or more, relative to the total weight of the composition.

The amount of the (a) cationic polysaccharide(s) in the composition according to the present invention may be 20% by weight or less, preferably 15% by weight or less, and more preferably 10% by weight or less, relative to the total weight of the composition.

The amount of the (a) cationic polysaccharide(s) in the composition according to the present invention may be from 0.01% to 20% by weight, preferably from 0.1% to 15% by weight, and more preferably from 0.5% to 10% by weight, relative to the total weight of the composition.

(Crosslinker)

The composition according to the present invention includes (b) at least one crosslinker having three or more acid groups or salt thereof. Two or more different types of (b) crosslinkers or salts thereof may be used in combination. Thus, a single type of (b) crosslinker or salt thereof or a combination of different types of (b) crosslinkers or salts thereof may be used.

At least one of the acid groups of the (b) crosslinker having three or more acid groups may be in the form of a salt. All the acid groups of the (b) crosslinker may be in the form of salts.

The term "salt" in the present specification means a salt formed by addition of suitable base(s) to the (b) crosslinker having three or more acid groups, which may be obtained from a reaction with the (b) crosslinker having three or more acid groups with the base(s) according to the methods known to those skilled in the art. As the salt, mention may be made of metal salts, for example salts with alkaline metal such as Na and K, and salts with alkaline earth metal such as Mg and Ca, and ammonium salts.

It is preferable that the (b) crosslinker be selected from non-polymeric acids having three or more acid groups, more preferably from non-polymeric organic acids having three or more acid groups.

The term "non-polymeric" here means that the (b) crosslinker is not obtained by polymerizing two or more monomers. Therefore, the non-polymeric acid, in particular the non-polymeric organic acid, does not correspond to an acid obtained by polymerizing two or more monomers such as polycarboxylic acid.

It is preferable that the molecular weight of the non-polymeric acid, in particular the non-polymeric organic acid, having three or more acid groups be 1000 or less, preferably 800 or less, and more preferably 600 or less.

The (b) crosslinker having three or more acid groups, or salt thereof, may be hydrophilic or water-soluble.

The (b) crosslinker having three or more acid groups may have three or more acid groups selected from the group consisting of a carboxylic group, a sulfuric group, a sulfonic group, a phosphonic group, phosphoric group, a phenolic hydroxyl group, and a mixture thereof.

The (b) crosslinker having three or more acid groups or salt thereof may be selected from the group consisting of tricarboxylic acids, tetracarboxylic acids, pentacarboxylic acids, hexacarboxylic acids, salts thereof, and mixtures thereof.

The (b) crosslinker having three or more acid groups or salt thereof may be selected from the group consisting of citric acid, aconitic acid, phytic acid, EDTA, glycyrrhizin, inositol triphosphate, inositol pentakisphosphate, tripolyphosphate, adenosine triphosphate, a salt thereof, and a mixture thereof.

It may be preferable that the (b) crosslinker having three or more acid groups or salt thereof be selected from the group consisting of citric acid, phytic acid, a salt thereof, and a mixture thereof.

The amount of the (b) crosslinker(s) having three or more acid groups or salt(s) thereof in the composition according to the present invention may be 0.001% by weight or more, preferably 0.05% by weight or more, and more preferably 0.1% by weight or more, relative to the total weight of the composition.

The amount of the (b) crosslinker(s) having three or more acid groups or salt(s) thereof in the composition according to the present invention may be 15% by weight or less, preferably 10% by weight or less, and more preferably 5% by weight or less, relative to the total weight of the composition.

The amount of the (b) crosslinker(s) having three or more acid groups or salt(s) thereof in the composition according to the present invention may be from 0.001% to 15% by weight, preferably from 0.05% to 10% by weight, and more preferably from 0.1% to 5% by weight, relative to the total weight of the composition.

(Physiologically Acceptable Volatile Medium)

The composition according to the present invention includes (c) at least one physiologically acceptable volatile medium.

The term "physiologically acceptable" volatile medium is intended to denote a volatile medium that is particularly suitable for applying the composition according to the present invention to keratin substance(s).

The term "volatile" means that the (c) physiologically acceptable medium can evaporate under a normal atmospheric pressure such as 1 atm and at room temperature such as 25° C.

The physiologically acceptable medium is generally adapted to the nature of the support onto which the composition according to the present invention is to be applied, and also to the form in which the composition according to the present invention is to be packaged.

The (c) physiologically acceptable volatile medium may comprise at least one hydrophilic organic solvent, water or a mixture thereof. It is preferable that the (c) physiologically acceptable volatile medium comprise water.

As the hydrophilic organic solvent, mention may be made of, for example, monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 8 carbon atoms, such as glycerol, propylene glycol, butylene glycol, pentylene glycol, hexylene glycol, caprylyl glycol, dipropylene glycol or diethylene glycol; glycol ethers (especially containing from 3 to 16 carbon atoms) such as mono-, di- or tripropylene glycol ($C_1$-$C_4$) alkyl ethers, mono-, di- or triethylene glycol ($C_1$-$C_4$)alkyl ethers, and mixtures thereof.

The amount of the (c) physiologically acceptable volatile medium, preferably water, in the composition according to the present invention may be 50% by weight or more, preferably 60% by weight or more, and more preferably 70% by weight or more, relative to the total weight of the composition.

The amount of the (c) physiologically acceptable volatile medium, preferably water, in the composition according to the present invention may be 99% by weight or less, preferably 98% by weight or less, and more preferably 97% by weight or less, relative to the total weight of the composition.

The amount of the (c) physiologically acceptable volatile medium, preferably water, in the composition according to the present invention may be from 50% to 99% by weight, preferably from 60% to 98% by weight, and more preferably from 70% to 97% by weight, relative to the total weight of the composition.

(Anionic Polymer)

The composition according to the present invention may include (d) at least one anionic polymer. Two or more different types of (d) anionic polymers may be used in combination. Thus, a single type of (d) anionic polymer or a combination of different types of (d) anionic polymers may be used.

An anionic polymer has a negative charge density. The charge density of the anionic polymer may be from 0.1 meq/g to 20 meq/g, preferably from 1 to 15 meq/g, and more preferably from 4 to 10 meq/g if the anionic polymer is a synthetic anionic polymer, and the average substitution degree of the anionic polymer may be from 0.1 to 3.0, preferably from 0.2 to 2.7, and more preferably from 0.3 to 2.5 if the anionic polymer is a natural anionic polymer.

It may be preferable that the molecular weight of the anionic polymer be 1,000 or more, preferably 10,000 or more, more preferably 100,000 or more, and even more preferably 1,000,000 or more.

The anionic polymer may have at least one negatively chargeable and/or negatively charged moiety selected from the group consisting of a sulfuric group, a sulfate group, a sulfonic group, a sulfonate group, a phosphoric group, a phosphate group, a phosphonic group, phosphoric group, a phosphonate group, a carboxylic group, and a carboxylate group.

The anionic polymer may be a homopolymer or a copolymer. The term "copolymer" is understood to mean both copolymers obtained from two kinds of monomers and those obtained from more than two kinds of monomers, such as terpolymers obtained from three kinds of monomers.

The anionic polymer may be selected from natural and synthetic anionic polymers.

The anionic polymer may comprise at least one hydrophobic chain.

The anionic polymer which may comprise at least one hydrophobic chain may be obtained by copolymerization of a monomer (a) chosen from carboxylic acids comprising α,β-ethylenic unsaturation (monomer a') and 2-acrylamido-2-methylpropanesulphonic acid (monomer a") with a non-surface-active monomer (b) comprising ethylenic unsaturation other than (a) and/or a monomer (c) comprising ethylenic unsaturation resulting from the reaction of an acrylic monomer comprising α,β-monoethylenic unsaturation or of an isocyanate monomer comprising monoethylenic unsaturation with a monohydric nonionic amphiphilic component or with a primary or secondary fatty amine.

Thus, the anionic polymer with at least one hydrophobic chain may be obtained by two synthetic routes:

either by copolymerization of the monomers (a') and (c), or (a'), (b) and (c), or (a") and (c), or (a"), (b) and (c), or by modification (and in particular esterification or amidation) of a copolymer formed from the monomers (a') or from the monomers (a') and (b), or (a") and (b), by a monohydric nonionic amphiphilic compound or a primary or secondary fatty amine.

Mention may in particular be made, as 2-acrylamido-2-methylpropanesulphonic acid copolymers, of those disclosed in the article "Micelle formation of random copolymers of sodium 2-(acrylamido)-2-methylpropanesulfonate and nonionic surfactant macromonomer in water as studied by fluorescence and dynamic light scattering—Macromolecules, 2000, Vol. 33, No. 10—3694-3704" and in applications EP-A-0 750 899 and EP-A-1 069 172.

The carboxylic acid comprising α,β-monoethylenic unsaturation constituting the monomer (a') can be chosen from numerous acids and in particular from acrylic acid, methacrylic acid, crotonic acid, itaconic acid and maleic acid. It is preferably acrylic or methacrylic acid.

The copolymer can comprise a monomer (b) comprising monoethylenic unsaturation which does not have surfactant property. The preferred monomers are those which give water-insoluble polymers when they are homopolymerized. They can be chosen, for example, from $C_1$-$C_4$ alkyl acrylates and methacrylates, such as methyl acrylate, ethyl acrylate, butyl acrylate or the corresponding methacrylates. The more particularly preferred monomers are methyl acrylate and ethyl acrylate. The other monomers which can be used are, for example, styrene, vinyltoluene, vinyl acetate, acrylonitrile and vinylidene chloride. Unreactive monomers are preferred, these monomers being those in which the single ethylenic group is the only group which is reactive under the polymerization conditions. However, monomers which comprise groups which react under the effect of heat, such as hydroxyethyl acrylate, can optionally be used.

The monomer (c) is obtained by reaction of an acrylic monomer comprising α,β-monoethylenic unsaturation, such as (a), or of an isocyanate monomer comprising monoethylenic unsaturation with a monohydric nonionic amphiphilic compound or a primary or secondary fatty amine.

The monohydric nonionic amphiphilic compounds or the primary or secondary fatty amines used to produce the nonionic monomer (c) are well known. The monohydric nonionic amphiphilic compounds are generally alkoxylated hydrophobic compounds comprising an alkylene oxide forming the hydrophilic part of the molecule. The hydrophobic compounds are generally composed of an aliphatic alcohol or an alkylphenol, in which compounds a carbonaceous chain comprising at least six carbon atoms constitutes the hydrophobic part of the amphiphilic compound.

The preferred monohydric nonionic amphiphilic compounds are compounds having the following formula (V):

$$R\text{—}(OCH_2CHR')_m\text{—}(OCH_2CH_2)_n\text{—}OH \quad (V)$$

in which R is chosen from alkyl or alkylene groups comprising from 6 to 30 carbon atoms and alkylaryl groups having alkyl radicals comprising from 8 to 30 carbon atoms, R' is chosen from alkyl groups comprising from 1 to 4 carbon atoms, n is a mean number ranging from approximately 1 to 150 and m is a mean number ranging from approximately 0 to 50, provided that n is at least as great as m.

Preferably, in the compounds of formula (V), the R group is chosen from alkyl groups comprising from 12 to 26 carbon atoms and alkylphenyl groups in which the alkyl group is $C_8$-$C_{13}$; the R' group is the methyl group; m=0 and n=1 to 25.

The preferred primary and secondary fatty amines are composed of one or two alkyl chains comprising from 6 to 30 carbon atoms.

The monomer used to form the nonionic urethane monomer (c) can be chosen from highly varied compounds. Use may be made of any compound comprising a copolymerizable unsaturation, such as an acrylic, methacrylic or allylic unsaturation. The monomer (c) can be obtained in particular from an isocyanate comprising monoethylenic unsaturation, such as, in particular, α,α-dimethyl-m-isopropenylbenzyl isocyanate.

The monomer (c) can be chosen in particular from acrylates, methacrylates or itaconates of oxyethylenated (1 to 50 EO) $C_6$-$C_{30}$ fatty alcohol, such as steareth-20 methacrylate, oxyethylenated (25 EO) behenyl methacrylate, oxyethylenated (20 EO) monocetyl itaconate, oxyethylenated (20 EO) monostearyl itaconate or the acrylate modified by polyoxyethylenated (25 EO) $C_{12}$-$C_{24}$ alcohols and from dimethyl-m-isopropenylbenzyl isocyanates of oxyethylenated (1 to 50 EO) $C_6$-$C_{30}$ fatty alcohol, such as, in particular, the dimethyl-m-isopropenylbenzyl isocyanate of oxyethylenated behenyl alcohol.

According to a specific embodiment of the present invention, the anionic polymer is chosen from acrylic terpolymers obtained from (a) a carboxylic acid comprising α,β-ethylenic unsaturation, (b) a non-surface-active monomer comprising ethylenic unsaturation other than (a), and (c) a nonionic urethane monomer which is the reaction product of a monohydric nonionic amphiphilic compound with an isocyanate comprising monoethylenic unsaturation.

Mention may in particular be made, as anionic polymers comprising at least one hydrophobic chain, of the acrylic acid/ethyl acrylate/alkyl acrylate terpolymer, such as the product as a 30% aqueous dispersion sold under the name Acusol 823 by Rohm & Haas; the acrylates/steareth-20 methacrylate copolymer, such as the product sold under the name Aculyn 22 by Rohm & Haas; the (meth)acrylic acid/ethyl acrylate/oxyethylenated (25 EO) behenyl methacrylate terpolymer, such as the product as an aqueous emulsion sold under the name Aculyn 28 by Rohm & Haas; the acrylic acid/oxyethylenated (20 EO) monocetyl itaconate copolymer, such as the product as a 30% aqueous dispersion sold under the name Structure 3001 by National Starch; the acrylic acid/oxyethylenated (20 EO) monostearyl itaconate copolymer, such as the product as a 30% aqueous dispersion sold under the name Structure 2001 by National Starch; the acrylates/acrylate modified by polyoxyethylenated (25 EO) $C_{12}$-$C_{24}$ alcohols copolymer, such as the 30-32% copolymer latex sold under the name Synthalen W2000 by 3V SA; or the methacrylic acid/methyl acrylate/dimethyl-meta-isopropenylbenzyl isocyanate of ethoxylated behenyl alcohol terpolymer, such as the product as a 24% aqueous dispersion and comprising 40 ethylene oxide groups disclosed in the document EP-A-0 173 109.

It may be preferable that the anionic polymer be selected from the group consisting of polysaccharides such as alginic acid, hyaluronic acid, and cellulose polymers (e.g., cellulose gum, hydroxyethylcellulose, hydroxypropylcellulose, methylcellulose, ethylhydroxyethylcellulose, and carboxymethylcellulose), anionic (co)polyamino acids such as (co)polyglutamic acids, (co)poly(meth)acrylic acids, (co)polyamic acids, (co)polystyrene sulfonate, (co)poly(vinyl sulfates), dextran sulfate, chondroitin sulfate, (co)polymaleic acids, (co)polyfumaric acids, maleic anhydride (co)polymers, and salts thereof.

The maleic anhydride copolymer may comprise one or more maleic anhydride comonomers, and one or more comonomers chosen from vinyl acetate, vinyl alcohol, vinylpyrrolidone, olefins comprising from 2 to 20 carbon atoms, and styrene.

Thus, the "maleic anhydride copolymer" is understood to mean any polymer obtained by copolymerization of one or more maleic anhydride comonomers and of one or more comonomers chosen from vinyl acetate, vinyl alcohol, vinylpyrrolidone, olefins comprising from 2 to 20 carbon atoms, such as octadecene, ethylene, isobutylene, diisobutylene or isooctylene, and styrene, the maleic anhydride comonomers optionally being partially or completely hydrolysed. Use will preferably be made of hydrophilic polymers, that is to say polymers having a solubility of water of greater than or equal to 2 g/l.

It may be preferable to use copolymers obtained by copolymerization of one or more maleic anhydride units of which the maleic anhydride units are in the hydrolysed form, and more preferably in the form of alkaline salts, for example in the form of ammonium, sodium, potassium or lithium salts.

In an advantageous aspect of the present invention, the maleic anhydride copolymer may have a molar fraction of maleic anhydride units of between 0.1 and 1, more preferably between 0.4 and 0.9.

The weight-average molar mass of the maleic anhydride copolymer may be between 1,000 and 500,000, and preferably between 1,000 and 50,000.

It is preferable that the maleic anhydride copolymer be a styrene/maleic anhydride copolymer, and more preferably sodium styrene/maleic anhydride copolymer.

Use will preferably be made of a copolymer of styrene and of maleic anhydride in a 50/50 ratio.

Use may be made, for example, of the styrene/maleic anhydride (50/50) copolymer, in the form of an ammonium salt at 30% in water, sold under the reference SMA1000H® by Cray Valley or the styrene/maleic anhydride (50/50) copolymer, in the form of a sodium salt at 40% in water, sold under the reference SMA1000HNa® by Cray Valley.

The amount of the anionic polymer(s) in the composition according to the present invention may be from 0.001% by weight or more, preferably 0.01% by weight or more, and more preferably from 0.1% by weight or more, relative to the total weight of the composition.

The amount of the anionic polymer(s) in the composition according to the present invention may be from 20% by weight or less, preferably from 15% by weight or less, and more preferably from 15% by weight or less, relative to the total weight of the composition.

The amount of the anionic polymer(s) in the composition according to the present invention may be from 0.001% to 20% by weight, preferably from 0.01% to 15% by weight, and more preferably from 0.1% to 15% by weight, relative to the total weight of the composition.

(Cosmetic Active Ingredient)

The composition according to the present invention may comprise at least one cosmetic active ingredient. There is no limitation to the cosmetic active ingredient. Two or more cosmetic active ingredients may be used in combination. Thus, a single type of cosmetic active ingredient or a combination of different types of cosmetic active ingredients may be used.

Among the cosmetic active ingredients to be used, mention may be made of UV filters, anti-oxidants, cleansing agents, free radical scavengers, moisturizers, whitening agents, liporegulators, anti-acne agents, antidandruff agents, anti-aging agents, softeners, anti-wrinkle agents, keratolitic agents, anti-inflammatory agents, fresheners, healing agents, vascular protectors, antibacterial agents, antifungal agents, antiperspirants, deodorants, skin conditioners, anesthetics, immunomodulators, nourishing agents, and sebum absorbers or moisture absorbers.

It is preferable that the (b) crosslinker be able to function as a cosmetic active agent. If the (b) crosslinker can function as a cosmetic active agent, it may not be necessary for the composition according to the present invention to include cosmetic active agent(s).

The composition according to the present invention may comprise the cosmetic active ingredient(s) in an amount of from 0.01% to 25% by weight, preferably from 0.1% to 20% by weight, more preferably from 1% to 15% by weight, and even more preferably from 2% to 10% by weight, relative to the total weight of the composition.

UV Filter

According to a preferred embodiment of the present invention, the cosmetic active ingredient may be selected from UV filters.

There is no limit to the type of UV filter. Two or more types of UV filters may be used in combination. Thus, a single type of UV filter or a combination of different types of UV filters may be used. The UV filter can be selected from the group consisting of an inorganic UV filter, an organic UV filter, and a mixture thereof.

Inorganic UV Filter

The composition according to the present invention may comprise at least one inorganic UV filter. If two or more inorganic UV filters are used, they may be the same or different, preferably the same.

The inorganic UV filter used for the present invention may be active in the UV-A and/or UV-B region. The inorganic UV filter may be hydrophilic and/or lipophilic. The inorganic UV filter is preferably insoluble in solvents such as water and ethanol commonly used in cosmetics.

It is preferable that the inorganic UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic UV filter can be selected from the group consisting of silicon carbide, metal oxides which may or may not be coated, and mixtures thereof.

Preferably, the inorganic UV filters may be selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, which are all UV photoprotective agents that are well known per se. Preferably, the inorganic UV filters may be selected from titanium oxide, zinc oxide, and more preferably titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl)Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes, and polyalkylhydrosiloxanes. More preferably still, the silicones are selected from the group consisting of octyltrimethylsilanes, polydimethylsiloxanes, and polymethylhydrosiloxanes.

Of course, the inorganic UV filters made of metal oxides may, before their treatment with silicones, have been treated with other surfacing agents, in particular, with cerium oxide, alumina, silica, aluminum compounds, silicon compounds, or their mixtures.

The coated inorganic UV filter may have been prepared by subjecting the inorganic UV filter to one or more surface treatments of a chemical, electronic, mechanochemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filters may be titanium oxides coated with:

silica, such as the product "Sunveil" from Ikeda;

silica and iron oxide, such as the product "Sunveil F" from Ikeda;

silica and alumina, such as the products "Microtitanium Dioxide MT 500 SA" from Tayca, "Tioveil" from Tioxide, and "Mirasun TiW 60" from Rhodia;

alumina, such as the products "Tipaque TTO-55 (B)" and "Tipaque TTO-55 (A)" from Ishihara, and "UVT 14/4" from Kemira;

alumina and aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;

alumina and aluminum laurate, such as the product "Microtitanium Dioxide MT 100 S" from Tayca;

iron oxide and iron stearate, such as the product "Microtitanium Dioxide MT 100 F" from Tayca;

zinc oxide and zinc stearate, such as the product "BR351" from Tayca;

silica and alumina and treated with a silicone, such as the products "Microtitanium Dioxide MT 600 SAS", "Microtitanium Dioxide MT 500 SAS", and "Microtitanium Dioxide MT 100 SAS" from Tayca;

silica, alumina, and aluminum stearate and treated with a silicone, such as the product "STT-30-DS" from Titan Kogyo;

silica and treated with a silicone, such as the product "UV-Titan X 195" from Kemira;

alumina and treated with a silicone, such as the products "Tipaque TTO-55 (S)" from Ishihara or "UV Titan M 262" from Kemira;

triethanolamine, such as the product "STT-65-S" from Titan Kogyo;

stearic acid, such as the product "Tipaque TTO-55 (C)" from Ishihara; or sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, and anatase/ rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter:

Stearic acid (and) Aluminum Hydroxide (and) $TiO_2$, such as the product "MT-100 TV" from Tayca, with a mean primary particle diameter of 15 nm;

Dimethicone (and) Stearic Acid (and) Aluminum Hydroxide (and) $TiO_2$, such as the product "SA-TTO-S4" from Miyoshi Kasei, with a mean primary particle diameter of 15 nm;

Silica (and) $TiO_2$, such as the product "MT-100 WP" from Tayca, with a mean primary particle diameter of 15 nm;

Dimethicone (and) Silica (and) Aluminum Hydroxide (and) $TiO_2$, such as the product "MT-Y02" and "MT-Y-110 M3S" from Tayca, with a mean primary particle diameter of 10 nm;

Dimethicone (and) Aluminum Hydroxide (and) $TiO_2$, such as the product "SA-TTO-S3" from Miyoshi Kasei, with a mean primary particle diameter of 15 nm;

Dimethicone (and) Alumina (and) $TiO_2$, such as the product "UV TITAN M170" from Sachtleben, with a mean primary particle diameter of 15 nm; and Silica (and) Aluminum Hydroxide (and) Alginic Acid (and) $TiO_2$, such as the product "MT-100 AQ" from Tayca, with a mean primary particle diameter of 15 nm.

In terms of UV filtering ability, $TiO_2$ coated with at least one organic UV filter is more preferable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS", and by Tioxide under the trademark "Tioveil AQ".

The uncoated zinc oxide pigments are, for example:

those marketed under the trademark "Z-cote" by Sunsmart;

those marketed under the trademark "Nanox" by Elementis; and those marketed under the trademark "Nanogard WCD 2025" by Nanophase Technologies.

The coated zinc oxide pigments are, for example:

those marketed under the trademark "Oxide Zinc CS-5" by Toshiba (ZnO coated with polymethylhydrosiloxane);

those marketed under the trademark "Nanogard Zinc Oxide FN" by Nanophase Technologies (as a 40% dispersion in Finsolv TN, $C_{12}$-$C_{15}$ alkyl benzoate);

those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane);

those marketed under the trademark "NFD Ultrafine ZnO" by Daikin (ZnO coated with phosphate of perfluoroalkyl and a copolymer based on perfluoroalkylethyl as a dispersion in cyclopentasiloxane);

those marketed under the trademark "SPD-Z1" by Shin-Etsu (ZnO coated with a silicone-grafted acrylic polymer dispersed in cyclodimethylsiloxane);

those marketed under the trademark "Escalol Z100" by ISP (alumina-treated ZnO dispersed in an ethylhexyl methoxycinnamate/PVP-hexadecene copolymer/methicone mixture);

those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica, and with glycerol, such as the product "M 211" marketed by Kemira.

Coated inorganic UV filters are preferable, because the UV filtering effects of the inorganic UV filters can be enhanced. In addition, the coating(s) may help uniformly or homogeneously disperse the UV filters in the composition according to the present invention.

Organic UV Filter

The composition according to the present invention may comprise at least one organic UV filter. If two or more organic UV filters are used, they may be the same or different, preferably the same.

The organic UV filter used for the present invention may be active in the UV-A and/or UV-B region. The organic UV filter may be hydrophilic and/or lipophilic.

The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadiene compounds; guaiazulene and derivatives thereof; rutin and derivatives thereof; and mixtures thereof.

Mention may be made, as examples of the organic UV filter(s), of those denoted below under their INCI names, and mixtures thereof Anthranilic compounds: Menthyl anthranilate, marketed under the trademark "Neo Heliopan MA" by Haarmann and Reimer.

Dibenzoylmethane compounds: Butyl methoxydibenzoylmethane, marketed in particular under the trademark "Parsol 1789" by Hoffmann-La Roche; and isopropyl dibenzoylmethane.

Cinnamic compounds: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate (UVINUL A+ by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVINUL T150» by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184 and EP-893,119, and Drometrizole trisiloxane, marketed under the trademark "Silatrizole" by Rhodia Chimie or "Mexoryl XL" by L'Oreal, as represented below.

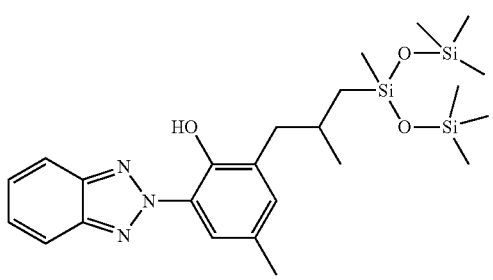 [SMILES: Cc1cc(CC(C)C[Si](C)(O[Si](C)(C)C)O[Si](C)(C)C)c(O)c(-n2nc3ccccc3n2)c1]

Benzoxazole compounds: 2,4-bis[5-1(dimethylpropyl) benzoxazol-2-yl-(4-phenyl)imino]-6-(2-ethylhexyl) imino-1,3,5-triazine, marketed under the trademark Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds: 1,1-dicarboxy(2,2'-dimethylpropyl)-4,4-diphenylbutadiene.

It is preferable that the organic UV filter(s) be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl)imino-1,3,5-triazine, camphor benzylkonium methosulfate and mixtures thereof.

The amount of the organic UV filter(s) in the composition according to the present invention may be less than 10% by weight, preferably less than 5% by weight, and more preferably less than 1% by weight, relative to the total weight of the composition The amount of the organic UV filter(s) in the composition according to the present invention may be 0.001% by weight or more, preferably 0.01% by weight or more, and more preferably 0.1% by weight or more, relative to the total weight of the composition.

(pH)

The pH of the composition according to the present invention may be from 3 to 9, preferably from 3.5 to 8, and more preferably from 4 to 7.

The pH of the composition may be adjusted by adding at least one alkaline agent and/or at least one acid. The pH of the composition may also be adjusted by adding at least one buffering agent.

(Alkaline Agent)

The composition according to the present invention may comprise at least one alkaline agent. Two or more alkaline agents may be used in combination. Thus, a single type of alkaline agent or a combination of different types of alkaline agents may be used.

The alkaline agent may be an inorganic alkaline agent. It is preferable that the inorganic alkaline agent be selected from the group consisting of ammonia; alkaline metal hydroxides; alkaline earth metal hydroxides; alkaline metal phosphates and monohydrogenophosphates such as sodium phosphate or sodium monohydrogeno phosphate.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As the inorganic alkaline agent, sodium hydroxide is preferable.

The alkaline agent may be an organic alkaline agent. It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof; polymers of basic amino acids and derivatives thereof; urea and derivatives thereof; and guanidine and derivatives thereof.

As examples of the organic alkaline agents, mention may be made of alkanolamines such as mono-, di- and tri-ethanolamine, and isopropanolamine; urea, guanidine and their derivatives;

basic amino acids such as lysine, ornithine or arginine; and diamines such as those described in the structure below:

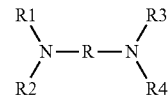

wherein R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Arginine, urea and monoethanolamine are preferable.

The alkaline agent(s) may be used in a total amount of from 0.001% to 10% by weight, preferably from 0.01% to 5% by weight, more preferably from 0.1% to 1% by weight, relative to the total weight of the composition, depending on their solubility.

(Acid)

The composition according to the present invention may comprise at least one acid. Two or more acids may be used in combination. Thus, a single type of acid or a combination of different types of acids may be used.

As the acid, mention may be made of any inorganic or organic acids which are commonly used in cosmetic products. A monovalent acid and/or a polyvalent acid may be used. A monovalent acid such as citric acid, lactic acid, sulfuric acid, phosphoric acid and hydrochloric acid (HCl) may be used. HCl is preferable.

The acid(s) may be used in a total amount of from 0.001% to 10% by weight, preferably from 0.01% to 5% by weight, more preferably from 0.1% to 1% by weight, relative to the total weight of the composition, depending on their solubility.

(Buffering Agent)

The composition according to the present invention may comprise at least one buffering agent. Two or more buffering agents may be used in combination. Thus, a single type of buffering agent or a combination of different types of buffering agents may be used.

As the buffering agent, mention may be made of an acetate buffer (for example, acetic acid+sodium acetate), a phosphate buffer (for example, sodium dihydrogen phosphate+di-sodium hydrogen phosphate), a citrate buffer (for example, citric acid+sodium citrate), a borate buffer (for example, boric acid+sodium borate), a tartrate buffer (for example, tartaric acid+sodium tartrate dihydrate), Tris buffer (for example, tris(hydroxymethyl)aminomethane), and Hepes buffer (4-(2-hydroxyethyl)-1-piperazineethanesulfonic acid).

(Optional Additives)

The composition according to the present invention may comprise, in addition to the aforementioned components, components typically employed in cosmetics, specifically, such as dyes, powders, oils, thickeners, organic non-volatile solvents, silicones and silicone derivatives, natural extracts derived from animals or vegetables, waxes, and the like, within a range which does not impair the effects of the present invention.

The composition according to the present invention may comprise the above optional additive(s) in an amount of from 0.001% to 10% by weight, preferably from 0.01% to 5% by weight, and more preferably from 0.1% to 1% by weight, relative to the total weight of the composition.

In one embodiment, the composition according to the present invention may include at least one oil. Two or more oils may be used in combination. Thus, a single type of oil or a combination of different types of oils may be used. Herein, the term "oil" is understood to mean a fatty substance which is liquid at ambient temperature (25° C.). The oil(s) may be volatile or non-volatile.

The amount of the oil(s) in the composition according to the present invention may be less than 10% by weight, preferably less than 5% by weight, and more preferably less than 1% by weight, relative to the total weight of the composition.

The amount of the oil(s) in the composition according to the present invention may be 0.001% by weight or more, preferably 0.01% by weight or more, and more preferably 0.1% by weight or more, relative to the total weight of the composition.

[Composition]

The composition according to the present invention may be intended to be used as a cosmetic composition. Thus, the cosmetic composition according to the present invention may be intended for application onto a keratin substance. Keratin substance here means a material containing keratin as a main constituent element, and examples thereof include the skin, scalp, nails, lips, hair, and the like. Thus, it is preferable that the cosmetic composition according to the present invention be used for a cosmetic process for the keratin substance, in particular skin.

Thus, the cosmetic composition according to the present invention may be a skin cosmetic composition, preferably a skin care composition or a skin makeup composition, in particular a composition for protecting skin from UV light and/or pollutants in the air.

The composition according to the present invention may be in any form such as a solution, a dispersion, an emulsion, a gel, and a paste. If the composition according to the present invention includes at least one oil and/or at least one organic UV filter, the composition according to the present invention may be in the form of an emulsion such as W/O, O/W, W/O/W and O/W/O, preferably, an O/W emulsion.

The composition according to the present invention can be prepared by mixing the above essential and optional ingredients in accordance with any of the processes which are well known to those skilled in the art.

The composition according to the present invention may include at least one surfactant. However, it is preferable that the amount of the surfactant(s) in the composition according to the present invention be limited.

The composition according to the present invention may optionally comprise at least one surfactant in an amount of 1% by weight or less, preferably 0.5% by weight or less, and more preferably 0.3% by weight or less, relative to the total weight of the composition.

In one embodiment, the composition according to the present invention is substantially free from surfactant. The term "substantially free from surfactant" means that the composition according to the present invention comprises no surfactant, or comprises at least one surfactant in an amount of 1% by weight or less, preferably 0.1% by weight or less, and more preferably 0.01% by weight or less, relative to the total weight of the composition.

The surfactant may be selected from the group consisting of anionic surfactants, amphoteric surfactants, cationic surfactants, and nonionic surfactants. Two or more surfactants may be used in combination. Thus, a single type of surfactant or a combination of different types of surfactants may be used.

[Film]

The composition according to the present invention can be used for easily preparing a self-healing or self-repairing film.

Thus, the present invention may also relate to a process for preparing a film, preferably a cosmetic film, comprising:

applying onto a substrate, preferably a keratin substrate, more preferably skin, the composition according to the present invention; and drying the composition.

Since the process for preparing a film according to the present invention includes the steps of applying the composition according to the present invention onto a substrate, preferably a keratin substrate, and more preferably skin, and of drying the composition, the process according to the present invention does not need any spin coating or spraying, and therefore, it is possible to easily prepare a film. Thus, the process for preparing a film according to present invention can prepare a film without any special equipment such as spin coaters and spraying machines.

The film may be thin and/or may be transparent, and therefore, may not be easy to perceive. Thus, the film may be used preferably as a cosmetic film.

If the substrate is not a keratin substrate such as skin, the composition according to the present invention may be applied onto a substrate made from any material other than keratin. The materials of the non-keratinous substrate are not limited. Two or more materials may be used in combination. Thus, a single type of material or a combination of different types of materials may be used. In any event, it is preferable that the substrate be flexible or elastic.

If the substrate is not a keratin substrate, it is preferable that the substrate be water-soluble, because it is possible to leave the film by washing the substrate with water. As examples of the water-soluble materials, mention may be made of poly(meth) acrylic acids, polyethyleneglycols, polyacrylamides, polyvinylalcohol (PVA), starch, cellulose acetates, and the like. PVA is preferable.

If the non-keratinous substrate is in the form of a sheet, it may have a thickness of more than that of the film according to the present invention, in order to ease the handling of the film attached to the substrate sheet. The thickness of the non-keratinous substrate sheet is not limited, but may be from 1 µm to 5 mm, preferably from 10 µm to 1 mm, and more preferably from 50 to 500 µm.

It is more preferable that the film be releasable from the non-keratinous substrate. The mode of release is not limited. Therefore, the film may be peeled from the non-keratinous substrate, or released by the dissolution of the substrate sheet into a solvent such as water.

The present invention may also relate to:

(1) A film, preferably a cosmetic film, prepared by a process comprising:
applying onto a substrate, preferably a keratin substrate, and more preferably skin, the composition according to the present invention; and
drying the composition,
and (2) A film, preferably a cosmetic film, comprising:
at least one cationic polysaccharide,
at least one crosslinker having three or more acid groups or salt thereof, and optionally at least one anionic polymer.

The above explanations for the ingredients in the composition according to the present invention can apply to the above cationic polysaccharide, the above crosslinker having three or more acid groups or salt thereof, and the above anionic polymer.

The film thus obtained above may be self-standing. The term "self-standing" here means that the film can be in the form of a sheet and can be handled as an independent sheet without the assistance of a substrate or support. Thus, the term "self-standing" may have the same meaning as "self-supporting".

The film may be used for cosmetic treatments of keratin substances, preferably skin, in particular the face. The film may be in any shape or form. For example, it can be used as a full-face mask sheet, or a patch for a part of the face such as the cheek, nose, and around the eyes.

[Cosmetic Process and Use]

The present invention also relates to:
a cosmetic process for a keratin substrate such as skin, comprising: applying to the keratin substrate the composition the present invention; and drying the composition to form a cosmetic film on the keratin substrate; and
a use of the composition according to the present invention for the preparation of a cosmetic film on a keratin substrate such as skin.

The cosmetic process here means non-therapeutic cosmetic method for caring for and/or making up the surface of a keratin substrate such as skin.

The above cosmetic film may have cosmetic effects such as absorbing or adsorbing malodor, changing the appearance of a keratin substrate such as skin, changing the feel to the touch of the keratin substrate, and/or protecting the keratin substrate from, for example, dirt or pollutants, due to the properties of the polyion complex particles in the cosmetic film, even if the cosmetic film does not include any cosmetic active ingredient.

In addition, the above cosmetic film may immediately change or modify the appearance of the skin by changing light reflection on the skin and the like, even if the cosmetic film does not include any cosmetic active ingredient. Therefore, it may be possible for the above cosmetic film to conceal skin defects such as pores or wrinkles. Further, the above cosmetic film may immediately change or modify the feel to the touch of the skin by changing the surface roughness on the skin and the like. Furthermore, the above cosmetic film may immediately protect the skin by covering the surface of the skin and shielding the skin, as a barrier, from environmental stresses such as pollutants, contaminants and the like.

The above cosmetic effects can be adjusted or controlled by changing the chemical composition, the thickness and/or the surface roughness of the above cosmetic film.

If the above cosmetic film includes at least one cosmetic active ingredient, the cosmetic film can have cosmetic effects provided by the cosmetic active ingredient(s). For example, if the cosmetic film includes at least one cosmetic active ingredient selected from anti-aging agents, anti-sebum agents, deodorant agents, anti-perspirant agents, whitening agents and a mixture thereof, the cosmetic film can treat the ageing of the skin, absorb sebum on the skin, control odors on the skin, control the perspiration on the skin, and/or whiten of the skin.

For example, if the cosmetic film includes a UV filter, the above cosmetic film may be able to limit the darkening of the skin, improve the colour and uniformity of the complexion, and/or treat aging of the skin.

It may also be possible to apply a makeup cosmetic composition onto the cosmetic film prepared by the present invention.

EXAMPLES

The present invention will be described in a more detailed manner by way of examples. However, they should not be construed as limiting the scope of the present invention.

Example 1

(Preparation of DIC-Gel Composed of 3 Components (CMC/PQ-67/Phytic Acid))

1.8 g of a 10 wt % aqueous solution of carboxymethylcellulose (CMC) as a polyanion, 0.79 g of polyquaternium-67 (PQ-67) as a polycation, 0.50 g of a 50 wt % aqueous solution of phytic acid as a cross-linker, 0.15 g of sodium hydroxide, and 96.76 g of water were mixed using a homogenizer. Thus, a stable translucent dispersion was successfully prepared. By evaporating water through heating, this dispersion was concentrated and a DIC-gel was prepared. The final solid concentration was about 10 wt %.

(Self-Healing Property Measurement of DIC-Gel)

The DIC-gel was cut into two pieces, and these were brought into contact in air at room temperature. After 1 hour, these two pieces adhered to each other.

Also, 1 ml of the DIC-gel translucent dispersion (before evaporating water) was applied onto a glass plate and dried at room temperature for 1 day to prepare a DIC-gel film. The surface of the DIC-gel film was scratched by a toothpick, and measured by confocal microscopy. On the film, a drop of water was poured and left to stand for 30 seconds. After removing the water, the surface was measured again. The trace of the scratch disappeared.

(Application of DIC-Gel for Smile Line Filling)

The concentrated DIC-gel was cut into small pieces and applied onto a smile line. The applied pieces were self-healed in the smile line, and merged each other. Finally, the smile line was varied with DIC-gel and the smile was not recognized well.

Example 2

(Preparation of DIC-Gel Emulsion)

0.593 g of Polyquaternium-67 and 0.135 g of cellulose gum were dissolved in 67.4 g of water (A1 phase), and 0.11 g of sodium hydroxide (A2 phase) was added into the mixture. 0.375 g of a 50 wt % phytic acid aqueous solution was diluted with 5 g of water (A3 phase), and this A3 phase was mixed with the above mentioned mixture to prepare a DIC-gel solution. Into this DIC-gel solution, water (A4 phase) was added. The preparation was carried out using a homogenizer. The oil phase (B) was emulsified with the DIC-gel solution at room temperature to prepare a DIC-gel emulsion.

The materials used to prepare the DIC-gel emulsion according to Example 2 are shown in Table 1. The numerical values for the amounts of the ingredients shown in Table 1 are all based on "% by weight".

TABLE 1

| Phase | Ingredients | Wt % |
| --- | --- | --- |
| A1 | Water | 67.4 |
|  | Polyquaternium-67 | 0.593 |
|  | Cellulose Gum | 0.135 |
| A2 | Sodium Hydroxide | 0.11 |
| A3 | Water | 5 |
|  | Phytic Acid | 0.1875 |
| A4 | Water | qsp 100 |
| B | Octocrylene | 5 |

(Self-Healing Property Measurement of DIC-Gel)

1 ml of the DIC-gel emulsion was applied onto a glass and dried at room temperature for 15 minutes to prepare a DIC-gel film. The surface of the DIC-gel film was scratched by a toothpick. The healing process of the scratched trace was checked by confocal microscopy.

The scratched trace was recovered.

Example 3

(Preparation of DIC-Gel Composed of 2 Components (PQ-67/Phytic Acid))

0.79 g of polyquaternium-67 (PQ-67) as a polycation, 0.50 g of a 50 wt % aqueous solution of phytic acid as a cross-linker, 0.15 g of sodium hydroxide, and 98.56 g of water were mixed using a homogenizer. Thus, a stable translucent dispersion was successfully prepared. By evaporating water through heating, this dispersion was concentrated and a DIC-gel was prepared. The final solid concentration was about 10 wt %.

(Self-Healing Property Measurement of DIC-Gel)

The concentrated DIC-gel was cut into two pieces, and these were brought into contact in air at room temperature. After 1 hour, these two pieces adhered to each other.

Also, 1 ml of the DIC-gel translucent dispersion (before evaporating water) was applied onto a glass plate and dried at room temperature for 1 day to prepare a DIC-gel film. The surface of the DIC-gel film was scratched by a toothpick, and measured by confocal microscopy. On the film, a drop of water was poured and left to stand for 30 seconds. After removing the water, the surface was measured again. The trace of the scratch disappeared.

Example 4

(Preparation of DIC-Gel Composed of 2 Components (PQ-10/Phytic Acid))

0.5 g of polyquaternium-10 was dissolved in 99.1 g of water, and 0.4 g of 50 wt phytic acid aqueous solution was mixed therein. Thus, a stable transparent dispersion was successfully prepared. By evaporating water through heating, this dispersion was concentrated and a DIC-gel was prepared. The final solid concentration was about 10 wt %.

(Self-Healing Property Measurement of DIC-Gel)

The DIC-gel was cut into two pieces, and these were brought into contact in air at room temperature. After 1 hour, these two pieces adhered to each other.

Also, 1 ml of the DIC-gel translucent dispersion (before evaporating water) was applied onto a glass plate and dried at room temperature for 1 day to prepare a DIC-gel film. The surface of the DIC-gel film was scratched by a toothpick, and measured by confocal microscopy. On the film, a drop of water was poured and left to stand for 30 seconds. After removing the water, the surface was measured again. The trace of the scratch disappeared.

Example 5

(Preparation of DIC-Gel Composed of 2 Components (PQ-67/Citric Acid))

0.55 g of polyquaternium-67, 0.24 g of citric acid was mixed with 95.79 g of water, and pH was adjusted to pH 7 with 10% sodium hydroxide solution. Thus, a stable transparent dispersion was successfully prepared. By evaporating water through heating, this dispersion was concentrated and a DIC-gel was prepared. The final solid concentration was about 10 wt %.

(Self-Healing Property Measurement of DIC-Gel)

1 ml of DIC-gel dispersion (before evaporating water) was applied onto a glass plate and dried at room temperature for 1 day to prepare a DIC-gel film. The surface of the DIC-gel film was scratched by a toothpick, and measured by confocal microscopy. On the film, a drop of water was poured and left to stand for 30 seconds. After removing the water, the surface was measured again. The trace of the scratch disappeared.

Example 6

(Preparation of DIC-Gel Composed of 2 Components (PQ-10/Citric Acid))

0.50 g of polyquaternium-10, 0.24 g of citric acid was mixed with 95.79 g of water, and pH was adjusted to pH 7 with 10% sodium hydroxide solution. Thus, a stable transparent dispersion was successfully prepared. By evaporating water through heating, this dispersion was concentrated and a DIC-gel was prepared. The final solid concentration was about 10 wt %.

(Self-Healing Property Measurement of DIC-Gel)

1 ml of DIC-gel dispersion (before evaporating water) was applied onto a glass plate and dried at room temperature for 1 day to prepare a DIC-gel film. The surface of the DIC-gel film was scratched by a toothpick, and measured by confocal microscopy. On the film, a drop of water was poured and left to stand for 30 seconds. After removing the water, the surface was measured again. The trace of the scratch disappeared.

Comparative Example 1

Polyquaternium-67 or polyquaternium-10 is originally a hydrogel if it is dissolved in water at the above-mentioned concentration. A hydrogel composed of polyquaternium-67 or polyquaternium-10 alone did not show the self-repairing property as shown below.

A concentrated hydrogel of polyquaternium-67 was cut into two pieces, and these were brought into contact in air at room temperature. After 1 hour, these two pieces did not adhere to each other.

Also, 1 ml of 0.79 wt % polyquaternium-67 aqueous solution was applied onto a glass plate and dried at room temperature for 1 day to prepare a polyquaternium-67 gel film. The surface of the polyquaternium-67 gel film was scratched by a toothpick, and measured by confocal microscopy. On the film, a drop of water was poured and left to stand for 30 seconds. After removing the water, the polyquaternium-67 gel film was partially dissolved into water and washed away, and self-repairing property was not recognized.

Comparative Example 2

1.8 g of a 10 wt % aqueous solution of carboxymethylcellulose (CMC) as a polyanion, 0.79 g of polyquaternium-67 (PQ-67) as a polycation, 0.50 g of a 50 wt % aqueous solution of phytic acid as a cross-linker, 0.15 g of sodium hydroxide, 0.50 g of phenoxyethanol, 3.33 g of a 33 wt % coco-betaine as a surfactant and 96.26 g of water were mixed using a homogenizer. Thus, a stable translucent dispersion was successfully prepared. By evaporating water through heating, this dispersion was concentrated and a DIC-gel was prepared. The final solid concentration was about 10 wt %.

The materials used to prepare the DIC-gel dispersion according to Comparative Example 2 are shown in Table 2. For convenience, the materials used to prepare the DIC-gel dispersion according to Example 1 are also shown in Table 2. The numerical values for the amounts of the ingredients shown in Table 2 are all based on "% by weight".

TABLE 2

| Ingredients | Example 1 | Comparative Example 2 |
| --- | --- | --- |
| Water | qsp 100 | qsp 100 |
| Polyquaternium-67 | 0.79 | 0.79 |
| Sodium Hydroxide | 0.15 | 0.15 |
| CMC | 1.80 | 1.80 |
| Phenoxyethanol | 0.50 | 0.50 |
| Coco-Betaine | — | 3.33 |
| Phytic Acid | 0.25 | 0.25 |

1 ml of the DIC-gel translucent dispersion (before evaporating water) according to Comparative Example 2 was applied onto a glass plate and dried at room temperature for 1 day to prepare a DIC-gel film. The surface of the DIC-gel film comprising the surfactant was scratched by a toothpick, and measured by confocal microscopy. On the film, a drop of water was poured and left to stand for 30 seconds. After removing the water, the film was partially dissolved into water and washed away, and self-repairing property was not recognized.

The invention claimed is:

1. A composition, comprising:
    (a) at least one cationic polysaccharide;
    (b) at least one crosslinker having three or more acid groups or salt thereof, and
    (c) at least one physiologically acceptable volatile medium, wherein the amount of the (a) cationic polysaccharide(s) in the composition is from 0.01% to 20% by weight, relative to the total weight of the composition;
    the (b) crosslinker(s) having three or more acid groups or salt thereof is selected from phytic acid and a salt thereof;
    the (b) crosslinker(s) having three or more acid groups or salt thereof ionically crosslinks the (a) cationic polysaccharide(s);
    wherein the (a) cationic polysaccharide(s) is selected from cationic hydroxyethylcellulose polymers;
    the composition optionally comprises surfactant(s) in an amount of 1% by weight or less, relative to the total weight of the composition, and
    the composition is capable of forming a self-healing or self-repairing film.

2. The composition according to claim 1, wherein the (a) cationic polysaccharide(s) has at least one quaternary ammonium group.

3. The composition according to claim 1, wherein the (a) cationic polysaccharide(s) is selected from the group consisting of polyquaternium-4, polyquaternium-10, polyquaternium-24, polyquaternium-67, and a mixture thereof.

4. The composition according to claim 1, wherein the amount of the (a) cationic polysaccharide(s) in the composition is from 0.10% to 15% by weight, relative to the total weight of the composition.

5. The composition according to claim 1, wherein the amount of the (b) crosslinker(s) having three or more acid groups or salt(s) thereof in the composition is from 0.001% to 15% by weight relative to the total weight of the composition.

6. The composition according to claim 1, wherein the amount of the (c) physiologically acceptable volatile medium(s), in the composition is from 50% to 99% by weight, relative to the total weight of the composition.

7. The composition according to claim 1, wherein the composition further comprises (d) at least one anionic polymer.

8. The composition according to claim 1, wherein the composition further comprises at least one oil and/or at least one organic UV filter.

9. The composition according to claim 8, wherein the amount of the oil(s) and/or the organic UV filter(s) in the composition is less than 10% by weight, relative to the total weight of the composition.

10. The composition according to claim 8, wherein the composition is in the form of an emulsion.

11. The composition according to claim 1, wherein the composition is a cosmetic composition.

12. A cosmetic process for a keratin substrate, comprising applying to the keratin substrate the composition according to claim 1; and
    drying the composition to form a cosmetic film on the keratin substrate,
    wherein the process is capable of forming a self-healing film or a self-repairing film.

* * * * *